United States Patent [19]
Haggerty et al.

[11] Patent Number: 5,416,577
[45] Date of Patent: May 16, 1995

[54] COLOR SENSOR FOR OPTICALLY MEASURING CONSISTING AND BRIGHTNESS OF MATERIALS

[75] Inventors: Alan L. Haggerty, Corcoran; Saad J. Bedros, West St. Paul; James E. Ingalls, Fridley; George F. Marschall, Roseville, all of Minn.

[73] Assignee: Honeywell Inc., Minneapolis, Minn.

[21] Appl. No.: 87,565

[22] Filed: Jul. 2, 1993

[51] Int. Cl.6 .................................................. G01J 3/28
[52] U.S. Cl. ..................................... 356/300; 356/328; 162/263
[58] Field of Search ............... 162/198, 258, 263, 238, 162/49; 356/326, 300, 328

[56] References Cited

U.S. PATENT DOCUMENTS

| | | |
|---|---|---|
| 3,962,581 | 6/1976 | Zimmerman . |
| 3,965,356 | 6/1976 | Howarth . |
| 3,968,006 | 7/1976 | Zimmerman . |
| 3,994,602 | 11/1976 | Howarth . |
| 4,040,743 | 8/1977 | Villaume et al. . |
| 4,171,916 | 10/1979 | Simms et al. . |
| 4,507,556 | 3/1985 | Brenholdt . |
| 4,838,692 | 6/1989 | Brenholdt . |
| 5,023,804 | 6/1991 | Hoult ................................. 356/303 |
| 5,042,948 | 8/1991 | Fletcher . |
| 5,044,753 | 9/1991 | Fletcher . |
| 5,082,370 | 1/1992 | Fletcher ............................ 356/328 |
| 5,115,811 | 5/1992 | Hartlaub et al. . |
| 5,157,465 | 10/1992 | Kronberg ........................... 356/405 |
| 5,243,546 | 9/1993 | Maggard ........................ 364/571.02 |

FOREIGN PATENT DOCUMENTS 1199813 1/1986 Canada .

OTHER PUBLICATIONS

Taina Sopenlehto-Pehkonen, "Mechanical Pulp Bleaching Control Based on In-Line Brightness and Residual Measurements", from the Canadian Pulp and Paper Association 1988 Annual Meeting.

Primary Examiner—F. L. Evans
Attorney, Agent, or Firm—Paul H. McDowall; Kenneth J. Johnson

[57] ABSTRACT

A method and apparatus for normalizing spectral data for an optical sensor. The sensor is comprised of a probe, a color sensor, a series of reflective targets, and a data processing means. Before the sensor is put into operation, a model is created, the use of which can normalize spectral data output by the color sensor for a variety of defined parameters. During operation of the sensor, the model maybe updated by rotating the targets individually in front of the probe. The targets have known reflectivities and the difference between the actual reflectivity and the spectral data is used to update the model.

19 Claims, 10 Drawing Sheets

COLOR SENSOR FOR OPTICALLY MEASURING CONSISTING AND BRIGHTNESS OF MATERIALS

This application is related to copending application Ser. No. 08/087,544, filed on even day herewith and assigned to the same assignee as the instant.

FIELD OF THE INVENTION

This invention relates to an optical sensor and more specifically to a method and apparatus for normalizing spectral data in an optical sensor.

BACKGROUND

Optical sensors are used in a variety of industrial applications. One such application is the production of paper. In the production of paper, several measurements are required during the manufacturing process to ensure consistent quality of the final product. Two such measurements are consistency and brightness.

During the manufacture of paper, wood fibers are separated from bulk wood by either mechanical or chemical means, or a combination. Water is then mixed with the wood fibers to form a wood pulp slurry. In order to achieve some measure of quality control during the process, it is essential to know the ratio of wood fibers to total mass (consistency) at every step in the process.

Some sensors used in the industry to measure consistency are mechanical in nature. One early method requires that a calibrated tapered rod about six inches long be dropped from a vertical position a standard distance above the stock. A reading is then taken of the depth the rod sinks in the stock. Other mechanical sensors, by one means or another, measure the force which moving pulp slurry produces on a mechanical arm, plate, or the like. Some limitations of these sensors are distortion due to velocity of the slurry, different wood species and drainage. Also such mechanical system cannot be readily installed in a tower or chamber through which pulp slurry is moving slowly or in which pulp slurry is contained. Finally, accuracy of mechanical sensors is limited for certain pulp consistencies.

The quality of paper is also dependent on the brightness of the pulp. Traditionally, brightness measurements are normally performed on an off-line basis. In this type of instrument, a sample is periodically taken from the pulp washer, dried, and its brightness determined from a reflectance meter. This determination can take 20 to 30 minutes.

Most modern methods of determining consistency and brightness of the pulp employ some means which emit radiant energy in the direction of the pulp. The magnitude of the energy which either passes through the pulp or is reflected back from the pulp is indicative of its brightness and consistency. This reflected energy can either be measured or compared to the magnitude of the energy emitted to determine the consistency and brightness of the pulp. The magnitude of the reflective energy can be separated into components for both consistency and brightness.

In an example of an on-line system, two sensors are positioned in the pulp to measure brightness of the pulp entering and leaving a bleaching stage. The two sensors measure the intensity of back scattered light and then compare results to control bleaching chemicals in order to optimize brightness of the pulp.

One drawback of the radiant energy methods is that as the sensor ages or certain conditions within the measurement chamber change, the sensor may output erroneous readings. There are mechanical systems which provide data normalization due to condition changes. In most cases, these mechanical systems extend out into the pulp flow and are susceptible to wear and premature failure from a variety of sources including vibration.

Therefore, providing data normalization which is less susceptible to vibration and does not require exposure to pulp has significant advantages.

SUMMARY

The invention herein is a method and apparatus for providing normalized data in an optical sensor. The apparatus comprises a light source, a receiver of reflected light, a light sensor, a plurality of reflectors of known and different reflectivities, and a data processor. Each reflector is rotatably mounted so as to individually pass in front of the light source and reflect light back into the receiver. The light sensor receives the light from the receiver and outputs at least one signal whose magnitude is proportional to the intensity of a particular wavelength of the reflected light. Within the data processor are components which normalize the signals output from the light sensor.

Data normalization is provided by establishing a at least one mathematical model through testing which relate the magnitude of spectrum output by the light sensor to the reflectivity of the pulp. The known reflectivities of the two reflectors are used to periodically update the mathematical models.

DESCRIPTION OF THE PREFERRED EMBODIMENT

Figure 1:
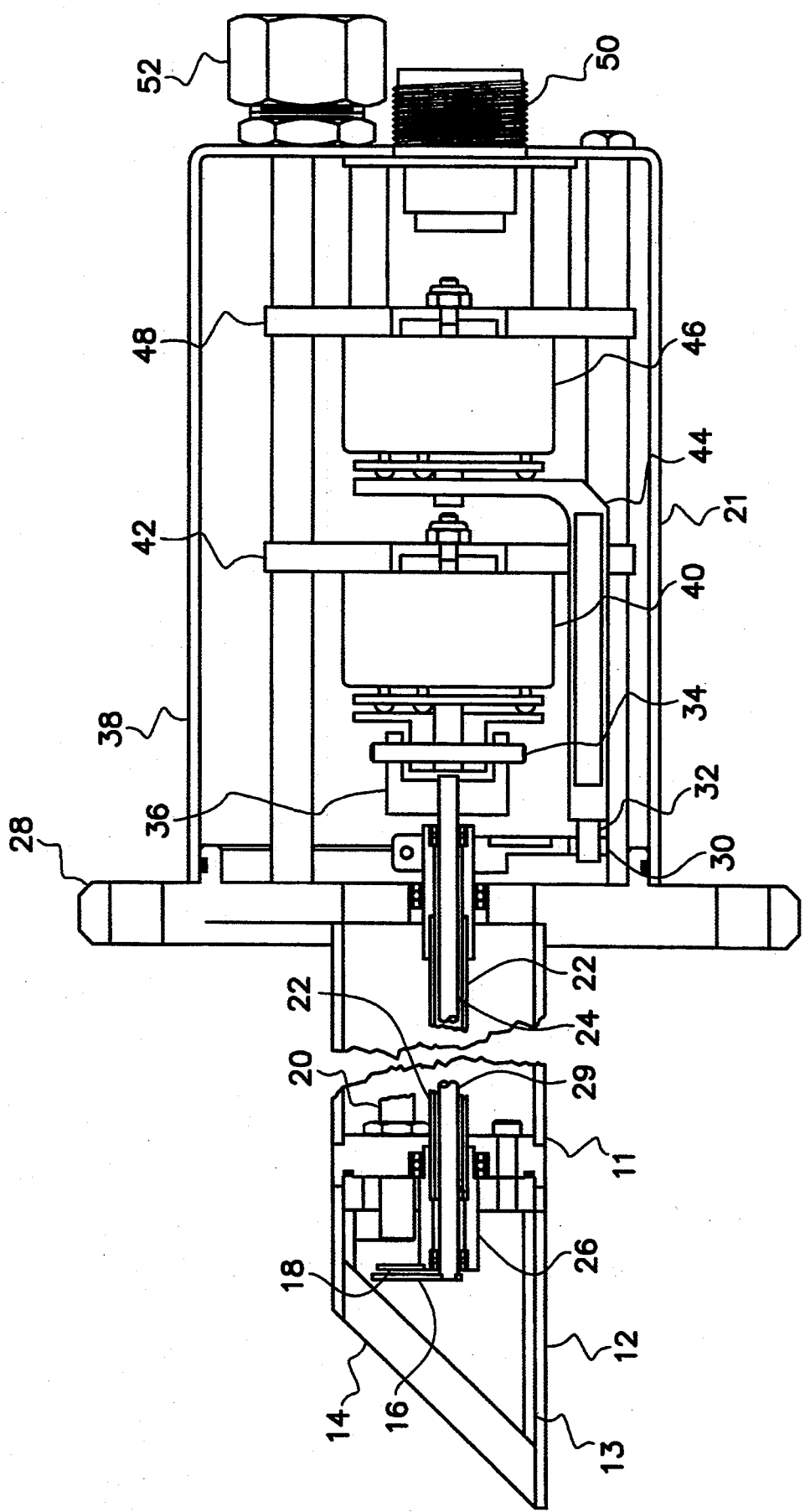
FIG. 1 is a cut-away view of the consistency and brightness sensor.

Disclosed in FIG. 1 is a preferred embodiment of sensor assembly 10. The major components of sensor assembly 10 are probe 11 and motor assembly 21. The probe 11 has a probe enclosure 12 with a window 14. Window 14 is made of a transparent material and is set at an angle to reduce reflectivity effects and improve flow characteristics over the probe. Within the enclosure is fiber-optic bundle 20 which has two functions. The bundle emits light which passes through the window 14, and then receives light which is reflected back. Also mounted within the probe enclosure are far target 16 and near target 18. The far target 16 is mounted on drive shaft 24 which passes from the probe to motor assembly 21. The near target 18 is mounted on adapter 26. The adapter 26 is mounted on the tube drive shaft 22 which encloses shaft 24. The tube drive shaft runs into the motor assembly 21. The tube shaft and drive shaft allow the targets 16 and 18 to rotate independent of each other. The targets are mounted so that they both rotate in front of the fiber-optic bundle 20.

Within the motor assembly 21, the drive shaft 24 is attached to outer coupling drive 36. The coupling drive 36 is connected to far target solenoid 40. The solenoid provides torque to rotate the far target. The tube drive shaft 22 is connected to near target arm 30. The near target arm is connected to near target solenoid arm 44 which in turn is connected to near target solenoid 46. Near target solenoid 46 provides torque to rotate near target 18. The solenoids 40 and 46 are mounted within the motor housing 38 by solenoids mounts 42 and 48, respectively. Power is provided to the solenoids through solenoid drive power connector 50. The fiber-optic bundles pass out of the motor housing through the fiber-optic strain relief 52. The sensor is mounted on a pulp container by use of the installation bracket 28.

Figure 2:
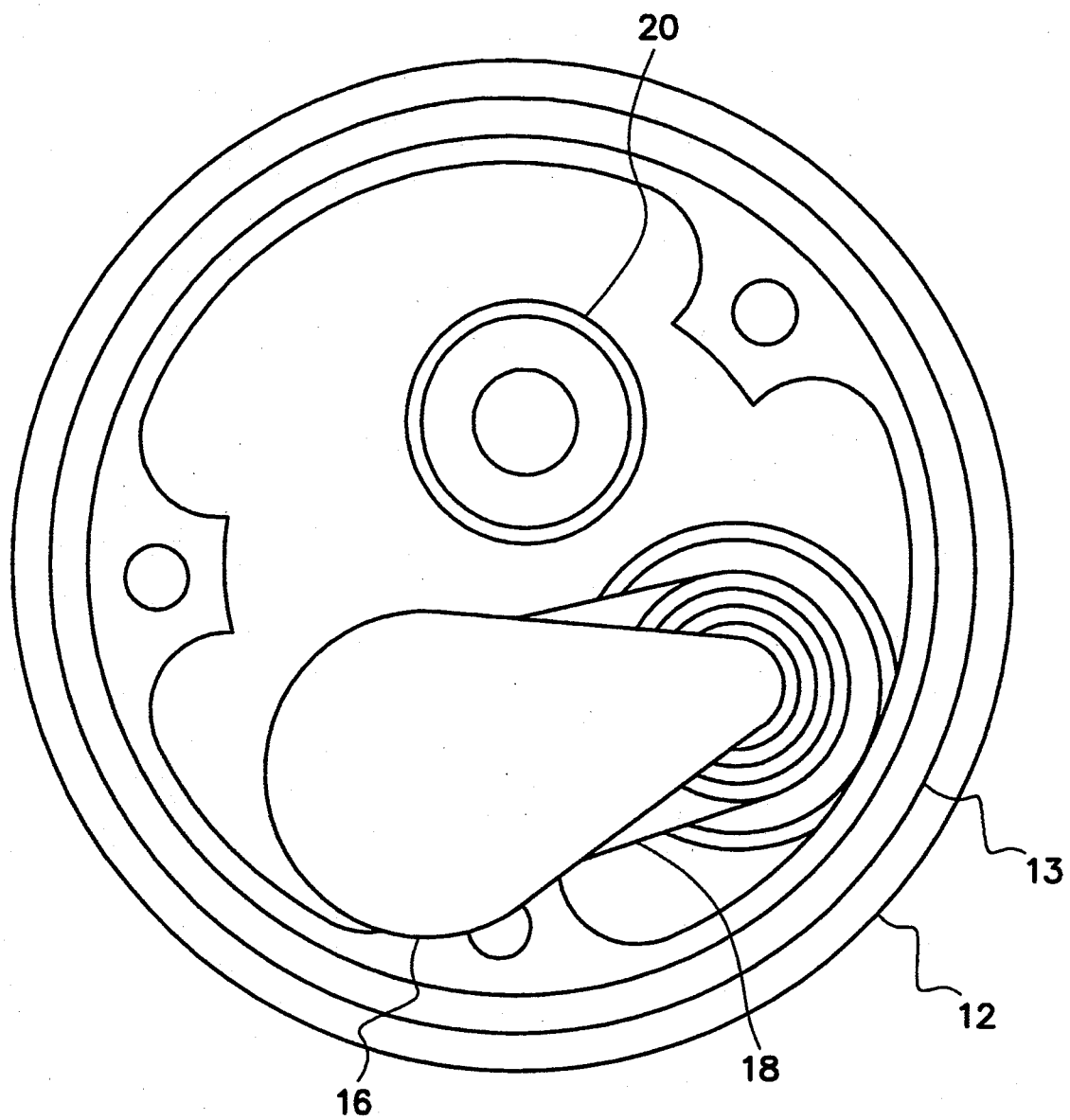
FIG. 2 is a front view of the probe, through the probe enclosure window.

FIG. 2 is an end view of the probe looking back through the window 14. As can be seen, targets 16 and 18 mounted so as to rotate up in front of the fiber-optic bundle 20 and then back again. Shown is the position of the targets when the probe is in its operational mode.

In another embodiment of the invention, only one reflector is rotably mounted proximate to the fiber optic bundle. In this embodiment, the reflector is laterally movable with respect to the fiber optic bundle 20. As the distance between the reflector and the fiber optic bundle changes, the amount of light reradiated into the bundle changes.

Figure 3A:
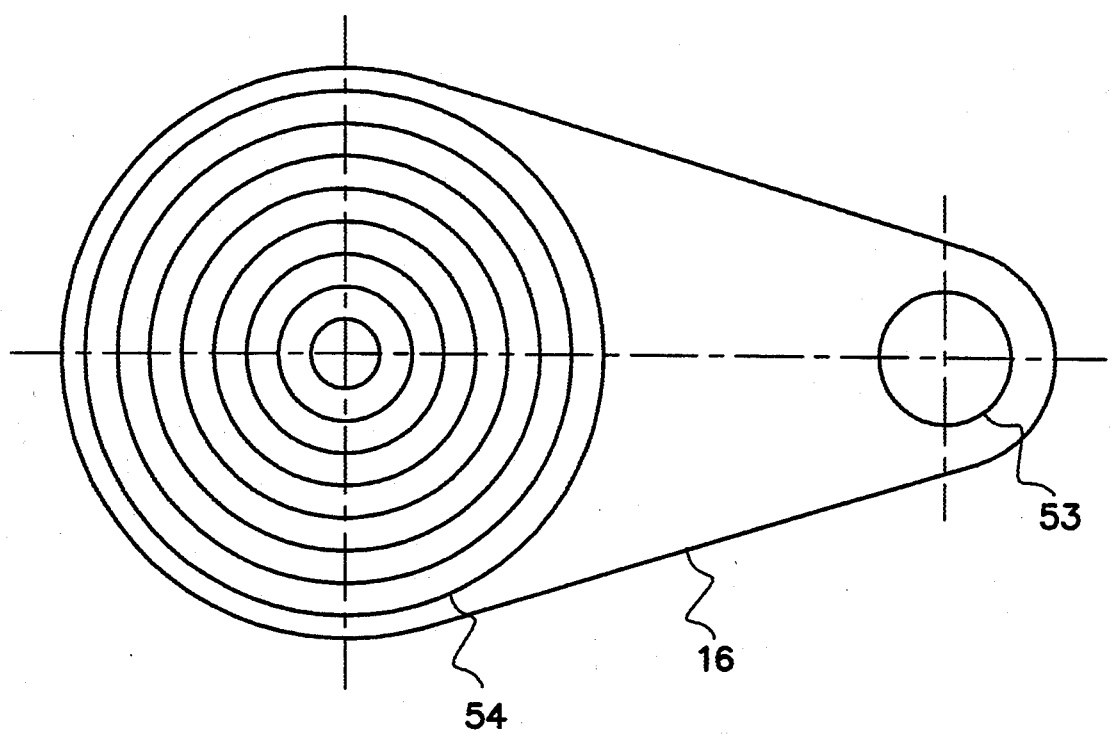
FIG. 3a is a top view of the far reflector and FIG. 3b is a cross sectional view of the far reflector.
Figure 3B:
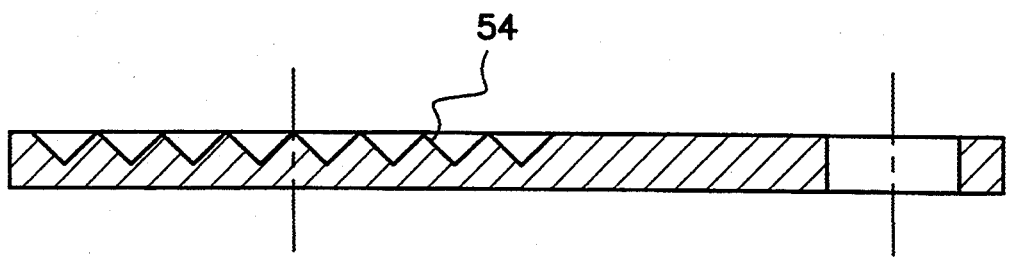
Figures 4A, 4B:
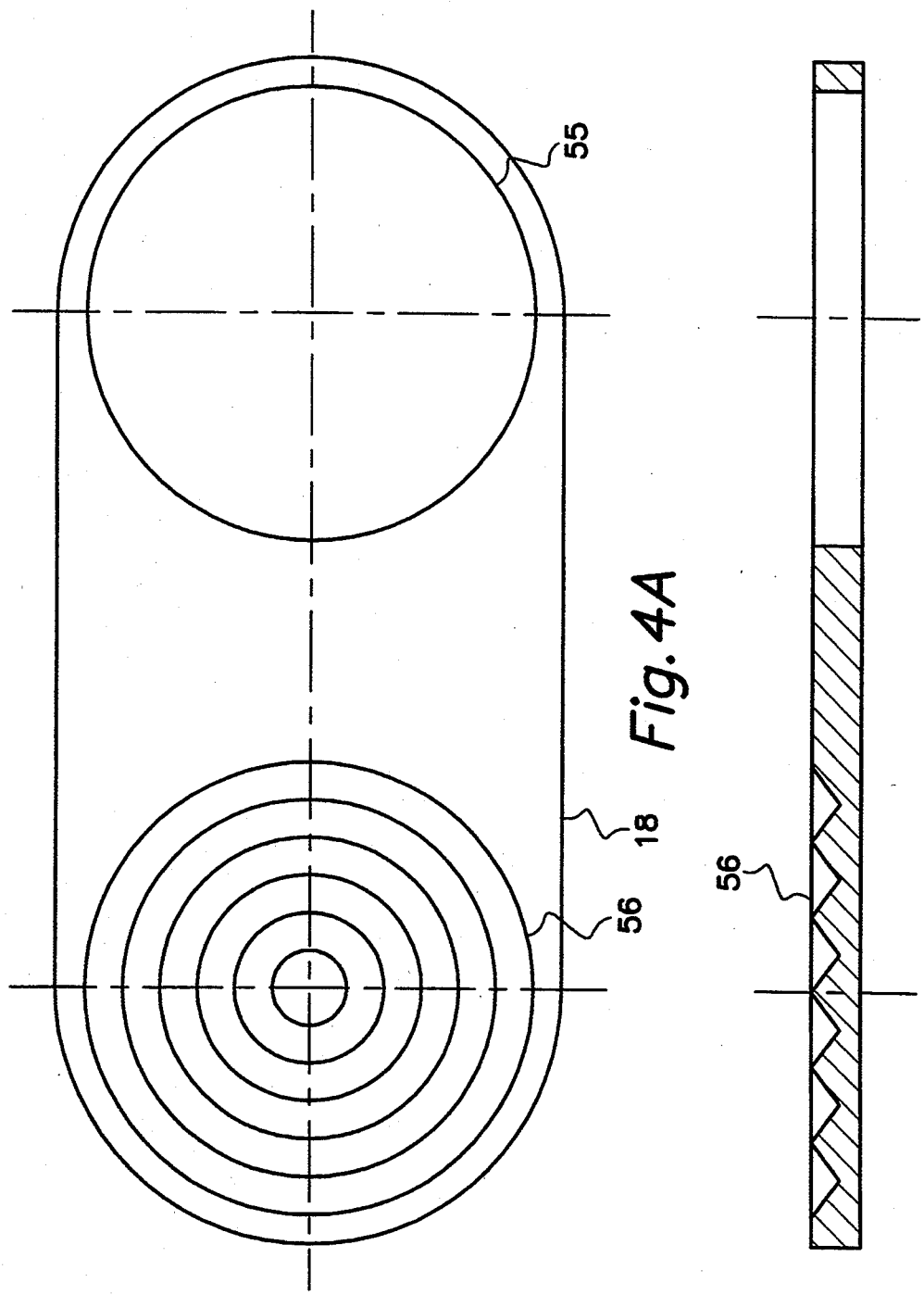
FIG 4a is a top view of the near reflector and FIG. 4b is cross sectional view of the near reflector.

Referring again to the preferred embodiment, shown in FIGS. 3a and 4a are top views of far target 16 and near target 18, respectively. On one end of the far target 16 is reflective area 54 and on the opposite end mounting hole 53 for mounting the target on the drive shaft 24. Near target 18 has reflective area 56 and mounting hole 55 for mounting on adapter 26. Each of the reflective areas 54 and 56 is of a known and different reflectivity. FIGS. 3b and 4b show a cross sectional view of the targets. The reflective areas 54 and 56 have a serrated shape to minimize mirror like reflections back to the fiber optic bundle. The serrated edges reradiate light in a diffuse manner to better indicate the actual reflectivity of the target.

This embodiment is most especially adapted to be used for pulp in papermaking. Where used for objects or other work substances, those of ordinary skill in the art can easily modify the structure to better reflect these operating conditions without going outside the scope of the claims of this invention.

Figure 5:
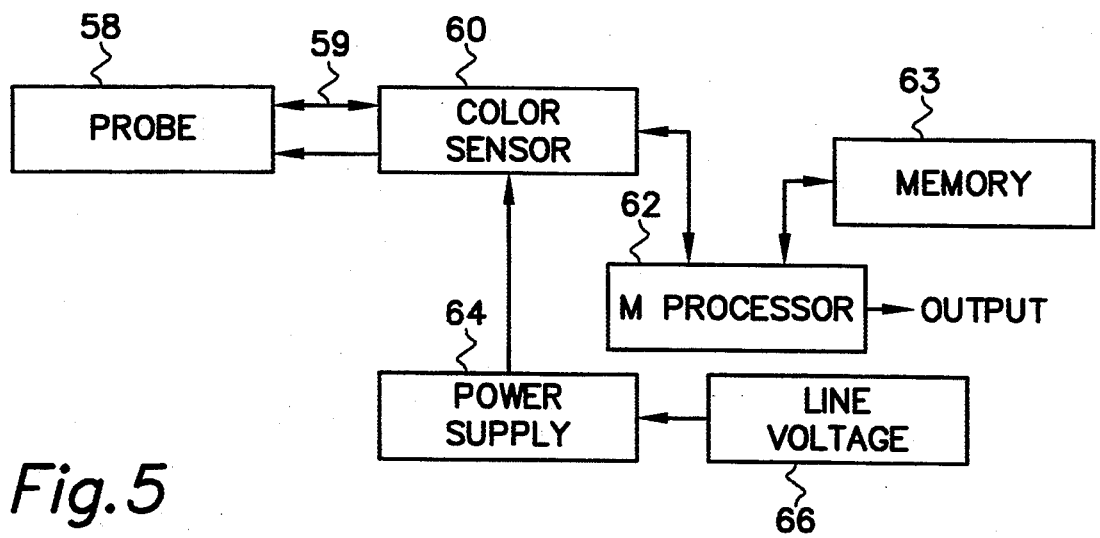
FIG. 5 is a block diagram of the brightness and consistency sensor.

Shown in FIG. 5 is a block diagram for components of the optical sensor. The probe 58, which is inserted into the pulp stream, radiates light. Some of the light is absorbed by the paper pulp and some reflected (thus it is re-radiated) with a high correlation to pulp consistency and brightness. The reflected light is collected by the probe and transmitted by fiber-optic cable 59 back to color sensor 60. The color sensor in this embodiment is a model manufactured by the Microswitch Company of Freeport, Ill. The color sensor generates a 128×1 color spectrum over the visible light wavelength range (400 to 800 NM). Although the visible light range is used in this preferred embodiment, it is possible that other wavelength ranges which extend over other domains in the electromagnetic spectrum, such as ultraviolet and infrared, could be used. The color spectrum is transmitted by electronic signal to the microprocessor 62. The microprocessor is connected to memory/software 63. Power for the optical sensor is provided by line voltage 66 through power supply 64.

In an alternate embodiment of the invention, the targets are rotated manually, rather than through use of solenoids. This would provide a lower cost sensor and avoid any reliability problems due to the operation of electric motors in a hostile environment.

Figure 6:
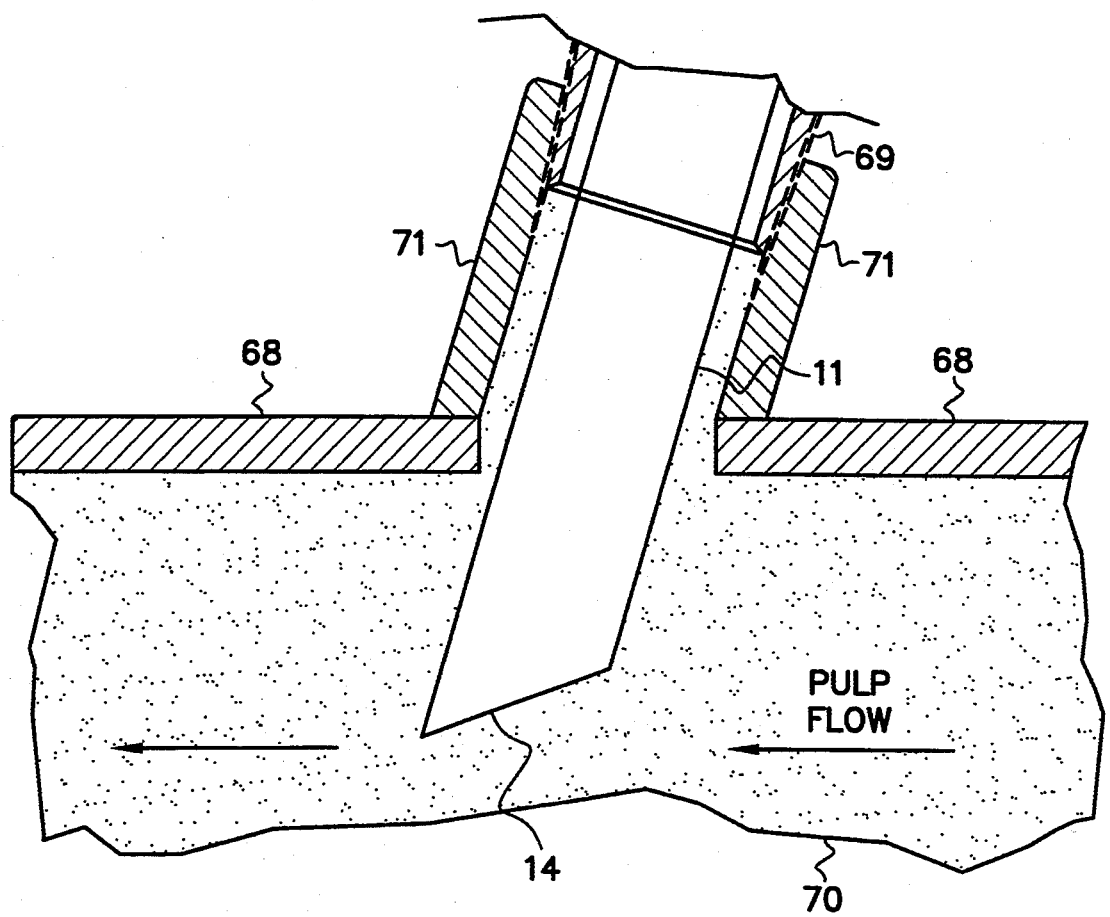
FIG. 6 is a diagram of the brightness and consistency sensor inserted in the pulp flow.

The operation of the optical sensor can be better understood by study of FIG. 6. As is shown, the optical sensor 10 is mounted on pulp container 68. In this preferred embodiment, the probe is held in threaded coupler 69 and is attached to the container 68 by mating the coupler 69 with extension 71. Depending on the condition which is being monitored, the sensor can be mounted anywhere along the production equipment where the paper is in pulp form. As is seen, the probe extends out into the pulp flow 70. Moving pulp passes around the probe and over the window 14. Light from within the probe shines through window 14 and reflects off the pulp. Light reflected back into the probe enclosure is received by fiber optic bundle 20 and transmitted to the systems electronics. The system electronics converts the fiber optic signal transmitted over the bundle into electronic signals representative of the brightness and consistency of the pulp.

Figure 7:
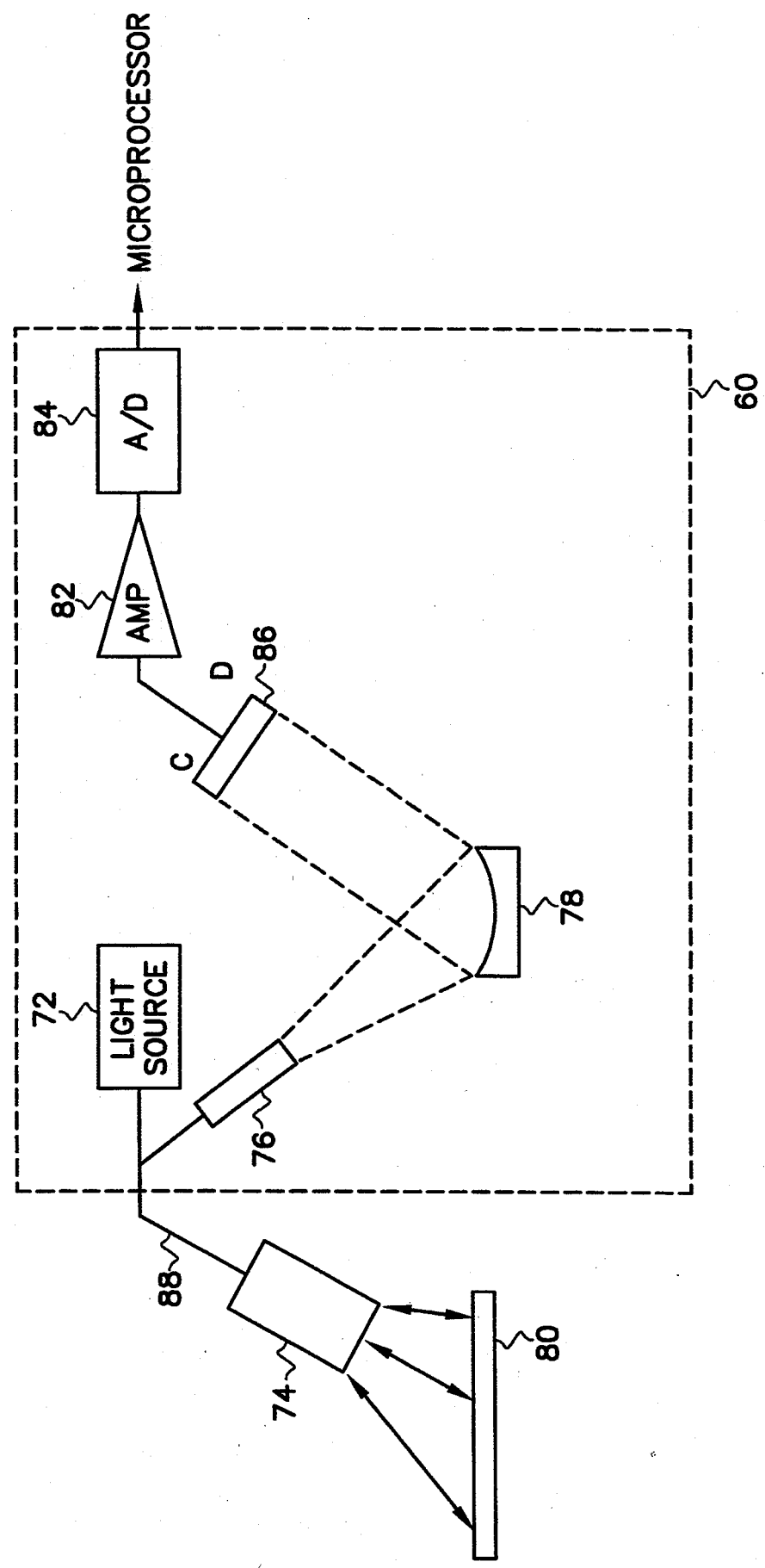
FIG. 7 is a diagram of the color sensor.

An important feature of the present invention is the intensity measurements of the reflected light made over substantially the entire visible light bandwidth region. The preferred color sensor 60 utilizes the complete visible spectrum rather than a few discreet wavelengths. The operation of the color sensor can be better understood by study of FIG. 7. In the presently preferred embodiment, light emitting/receiving end 74 performs a dual purpose of both emitting light and receiving back the reflective light. Light to be emitted is transmitted from a light source 72 through fiber optic line 88 to the light emitting/receiving end 74. Light is reflected off the object 80 and then back into the light emitting/receiving end 74. Reflected light is carried by fiber optic line 88 to disbursing element 78. On one end of fiber optic line 88 is light exiting end 76. Reflected light leaving light exiting end 76 strikes disbursing element 78. Disbursing element 78 may be a diffraction grading. The reflected light is broken into its component wavelength and reflected to detector array 86. For this embodiment, disbursing element 78 disburses and provides a flat field of focus of the spectrum (400 NM to 800 NM) on detector array 86. The focus spectrum strikes detector array 86 with 400 NM light at side C and 800 NM light at side D.

Light disbursed and reflected by disbursing element 78 is directed toward a detector array 86. Detector array 86 may be comprised of a linear sequence of N photodetectors. For this embodiment, N=128. Each photodetector is adapted to produce an electrical signal when light of a predetermined frequency impinges thereon. The magnitude of the signal is directly proportional to the intensity of the light which strikes the photodetector.

The magnitude of the signal output from the color sensor may be affected by another factor. Within the color sensor electronics controls the amount of time the photodetectors are exposed to light. The period of exposure is known as integration time. As the integration time increases, the magnitude of the signal output from the color sensor increases. When the integration time decreases, the magnitude of the signal decreases. In order to get accurate readings from the presently preferred embodiment, the integration time is held constant during operation of the color sensor.

The detector array produces an analog signal indicative of the color signature of object 80. The analog signal is amplified by amplifier 82 and then digitized by A/D converter 84, thus creating a 1×128 array of sensed component values. After digitization, the array of sensed values is transmitted to microprocessor 62.

During operation of the system, a variety of parameters may affect or influence the output of the color sensor. Four main parameters are:
reflectivity of target object
integration time of the detector array in a color sensor
ambient temperature of color sensor
color temperature and intensity of lamp Data normalization must be employed to control these parameter effects. The objective of normalization in the preferred embodiment is to determine an accurate reflectivity for spectral data of pulp using the color sensor under a variety of conditions. If the operating condition parameters were not taken into account, acquired spectra would vary so much as to not be useful in measuring pulp consistency and brightness.

In order to normalize the color sensor output, a normalization model must first be created. There are two steps in the development of a normalization model. The first step is to establish a model by testing the sensor at known reflectivity or direct light conditions. The output data, as the sensor input varies, will be predictable according to a model. Many techniques for modeling are known and may be used here.

In the second step, the now known or derived model along with the values of other parameters are used to solve for an unknown object or work piece reflectivity. The mathematical relationship for the normalization model is:

$$spec(\lambda) = f(r_t(\lambda), \tau, T_a, T_c)$$

Where:
spec ($\lambda$) = output spectrum of color sensor,
$r_t$ = reflectivity of target object,
$\tau$ = integration time of the detector array within the color sensor,
$T_a$ = ambient temperature of color sensor,
$T_c$ = color temperature and intensity of light source.

To develop the normalization equations, relationships must be established between color sensor output and influencing parameters. This is done either through experimentation or through performance information provided by the manufacturer of particular components of the sensor. For example, the Microswitch color sensor used in the presently preferred embodiment is known to respond in a linear fashion to changes in object reflectivity and detector array integration time.

According to this preferred embodiment, a linear term is added to the normalization model for the parameters of object reflectivity and integration time. The advantage of a linear model of behavior is that it can be easily updated.

Ambient temperature affects the behavior of the color sensor. The effect of these changes on the color sensor used has been determined by experiment and has been modeled by second order polynomial:

$$spec(\lambda) = c_2 T_a^2 + c_1 T_a + c_0$$

Where:
$T_a$ = ambient temperature.
$c_i$ = coefficients

The final parameter that affects the output of the color sensor is the color temperature and intensity of the lamp or light source within or used by the color sensor. It is known that the electrical current draw of the lamp is linearly related to its color temperature and intensity. For this reason, an electrical current sensor is included in the color sensor we used. The output of the current sensor is used to monitor the color sensor for changes in lamp intensity. Another second order polynomial was found to approximate the lamp current over the limited range of the visible spectra. This second order polynomial is $$spec(\lambda) = d_2 C^2 + d_1 C + d_0$$

Where:
C = current of lightsource
$d_i$ = coefficients

Output spectra of the color sensor were collected for different lamp color temperatures/currents by modifying the drive current of the lamp. These drive currents were used as the independent parameter in the normalization equation.

By combining the normalization equation for each of the parameters, the resulting normalization equation for the optical sensor is as follows:

$$spec(\lambda) = (a_1 r_t + a_0)(b_1 t + b_0)(c_2 T_a^2 + c_1 T_a + c_0)(d_2 C^2 + d_1 C + d_0)$$

Where:
spec ($\lambda$) = output spectrum of color sensor,
$r_t$ = reflectivity of target object,
t = integration time of the detector array of the color sensor,
$T_a$ = ambient temperature of color sensor,
C = current of light source.
$a_i, b_i, c_i, d_i$ = coefficients In order to use the normalization equations, the coefficients need to be established through testing or other provided information. In order to provide more flexibility in modeling, the equation is multiplied out to provide 36 different coefficients.

Figure 8:
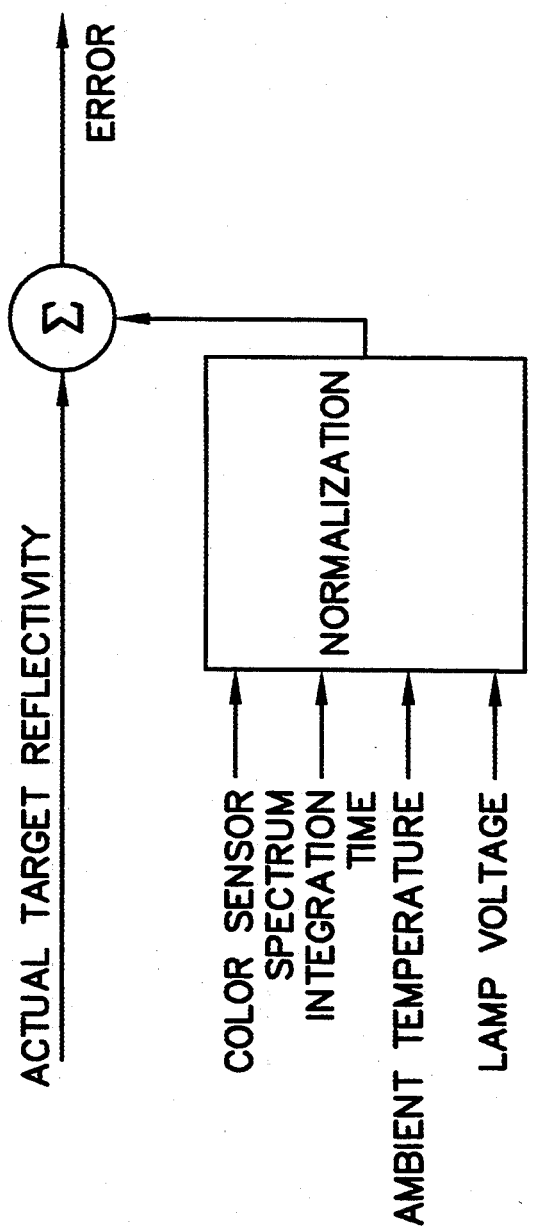
FIG. 8 is a control diagram for the normalization using just the first normalization equation.
Figure 9:
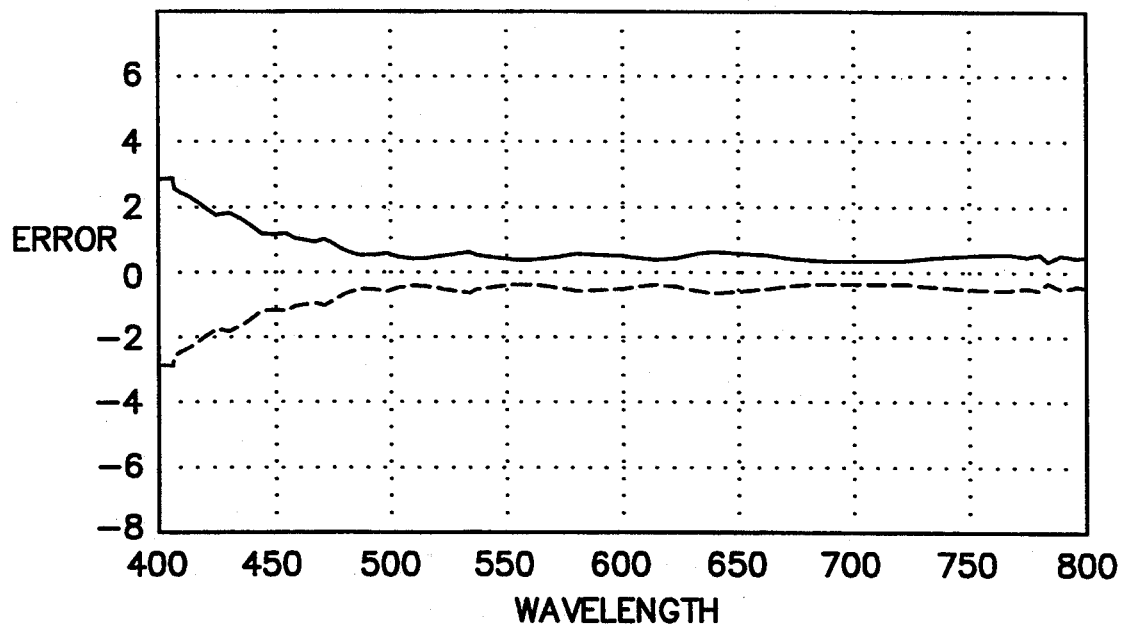
FIG. 9 is an error plot for color sensor No. 2 using normalization equation 2.
Figure 10:
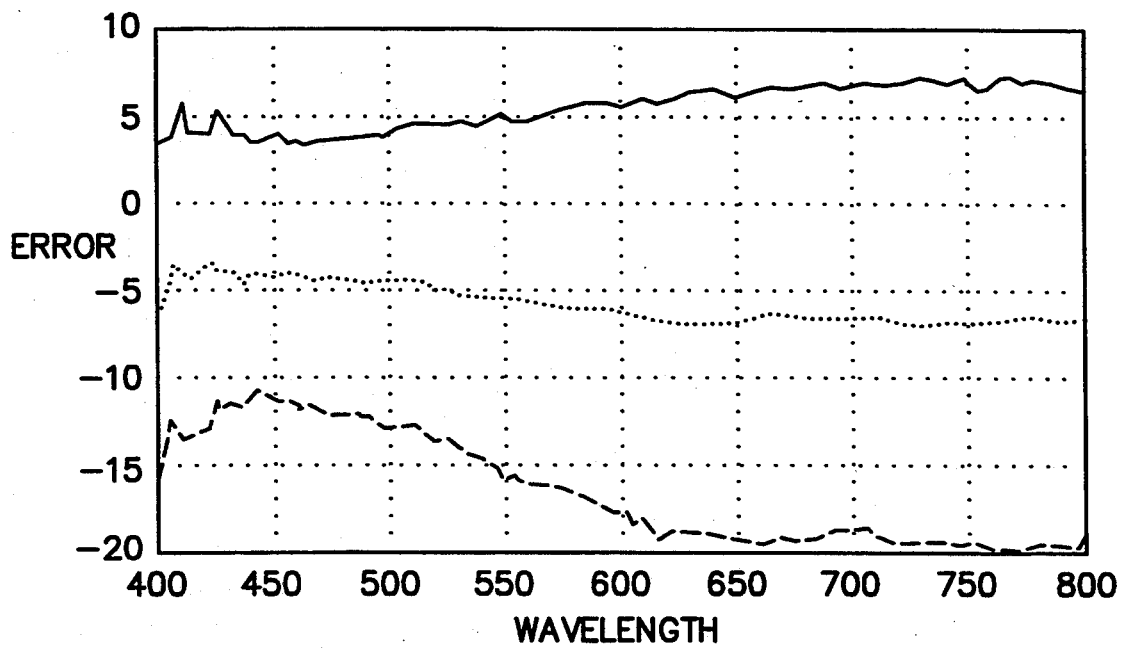
FIG. 10 is an error plot for color sensor No. 1 using normalization equation 2.

A representation of the implementation of the normalization equations is shown in the control diagram in FIG. 8. A model error is created between the normalization equation and a known target reflectivity. This model error is used to correct the coefficients of the normalization model. This technique provides compensation for the behavior of an individual color sensor. However, characterization of one color sensor will not perform well with a second color sensor. FIG. 9 shows an error plot of a second color sensor using normalization coefficients for the same sensor over the visible wavelength range. As can be seen, the error is very small. In FIG. 10, the error plot is of a first sensor using the normalization equation of the second sensor. In this case, the error is quite large. FIGS. 9 and 10 demonstrate that in order to get accurate readings, each color sensor should be characterized individually at the manufacturer of the color sensor to obtain the desired normalization performance.

A disadvantage of the normalization process described above is each parameter can prove to be expensive and time consuming to model. Prior to installation of the sensor in the field, it must go through a testing procedure in the laboratory in order to create the normalization model. If the unit is already in the field and the normalization model needs updating, the unit must be pulled out of service and returned to the lab. In the embodiment of the invention described below, a portion of the normalization model remains constant for all units in production, and an apparatus is provided for updating the normalization model while the optical sensor is in operation.

Figure 11:
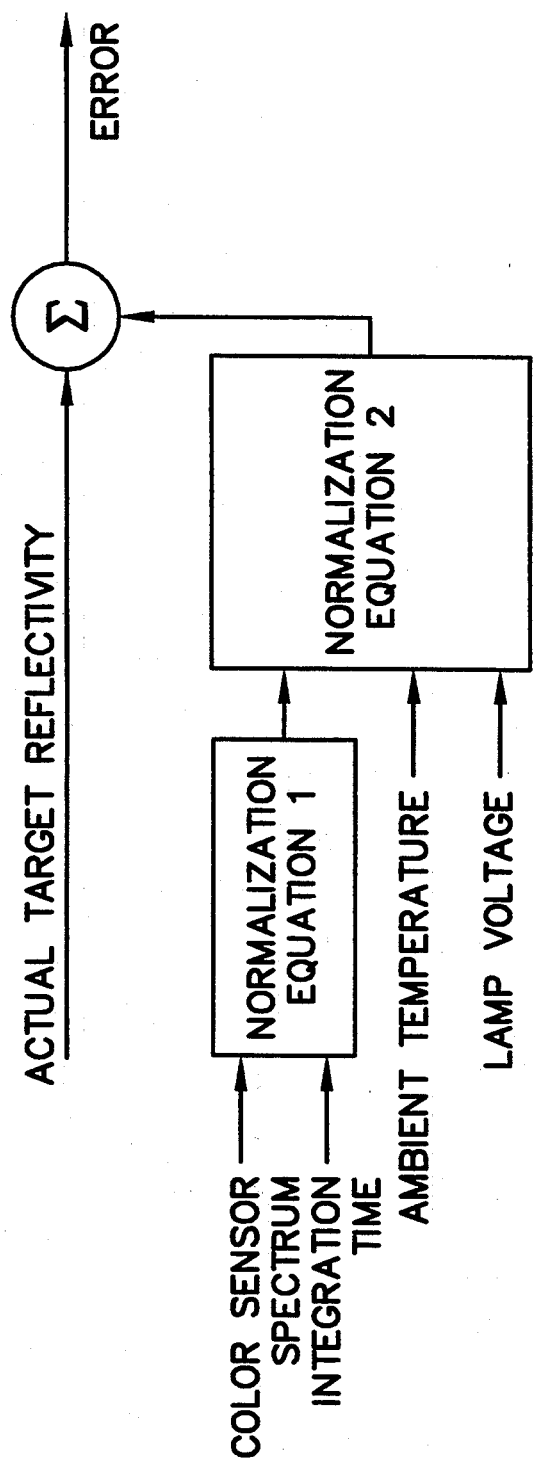
FIG. 11 is a control diagram for the normalization using both the first and second normalization equations.

The present normalization technique is depicted in the control diagram in FIG. 11. The equations depicted in the diagram are as follows:

$$\text{spec}(\lambda) = b_3 r_{int}(\lambda) t + b_2 r_{int}(\lambda) + b_1 t + b_0 \qquad \text{EQ.1}$$

Where:
$\tau$ = integration
spec $(\lambda)$ = output spectrum of color sensor
$r_{int}(\lambda)$ = intermediate spectral reflectivity
$b_i$ = coefficient $$r_{int}(\lambda) = (c_2 T_a^2 + c_1 T_a + c_0)(d_2 C^2 + d_1 C + d_0)(e_1 r(\lambda) + e_0) \qquad \text{EQ.2}$$

Where:
$r_{int}(\lambda)$ = intermediate spectral reflectivity
$r(\lambda)$ = spectral reflectivity of target object
$T_a$ = ambient temperature of color sensor
$C$ = current of light source
$c_i, d_i, e_i$ = coefficients In this technique, normalization equation 2 remains fixed for all time and all sensors. The coefficients in normalization equation 1 are adjusted to compensate for any differences between devices.

The input parameter variations required to determine model coefficients for normalization equation 1 are easy to obtain during manufacture and in the field. In contrast, the input parameter variation required to determine model coefficients for normalization equation 2 are expensive and time consuming to obtain. Therefore, the coefficients of normalization equation 2 will remain fixed. This equation can work because the principal difference between the output of two sensors without normalization models is an amplitude shift in the spectral intensity in response to differences in color temperature and ambient temperature. This amplitude shift can be corrected by adjusting the coefficients of normalization equation 1.

In actual operation, the model shown in EQ.2 is established through testing and provided for all color sensors. The adjustable coefficients for EQ.1 are then established for each of the color sensors. Once the models are created, the model coefficients are installed as part of the optical sensor and are ready for operation in the field. Once the optical sensor begins operating, the spectral data is output from the color sensor 60 and transmitted to the microprocessor 62. Stored in the memory 63 are the models for normalization of the spectral data.

Microprocessor 62 accesses these models and the data is normalized for the predicted parameters. The spectral data is then interpreted as pulp consistency and brightness by other components of the optical sensor.

From time to time, normalization equation 1 can be updated while the sensor is out in the field. As the optical sensor operates, the performance of the system may change in ways not predicted by the models. This requires that the normalization models be periodically updated. By providing two known reflectivities, the slope and y-intersect of the linear relationship in EQ.1 can be updated.

As was described above, targets 16 and 18 have areas of known reflectivity. In order to update the normalization models in the memory 63, each target is individually rotated in front of the fiber optic bundle and multiple readings are taken for different integration times. The two reflectivities taken provide two points of spectrum output vs. reflectivity. From the measured data, a linear relationship is then established and the normalization model is updated. Once the readings are taken, the targets are rotated back to a position where they do not interfere with light reflected from the pulp. One advantage of the present invention is that the consistency and brightness sensor does not have to be removed from service in order to update the normalization model. While the probe is still immersed in the pulp, the solenoids 40 and 46 are electrically actuated and they provide torque to rotate targets 16 and 18. The targets may also be manually actuated. Because all the mechanical systems are contained within the probe enclosure, there is no possibility that the pulp flow will cause any degradation of the system.

Figure 12:
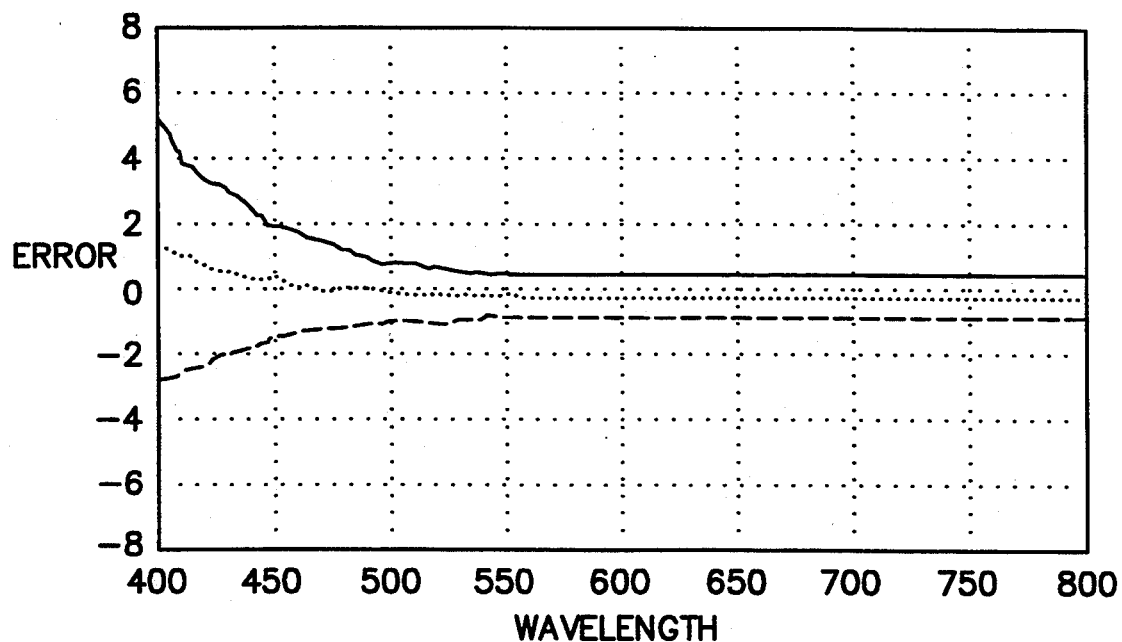
FIG. 12 is an error plot for color sensor No. 1 using normalization technique No. 2.
Figure 13:
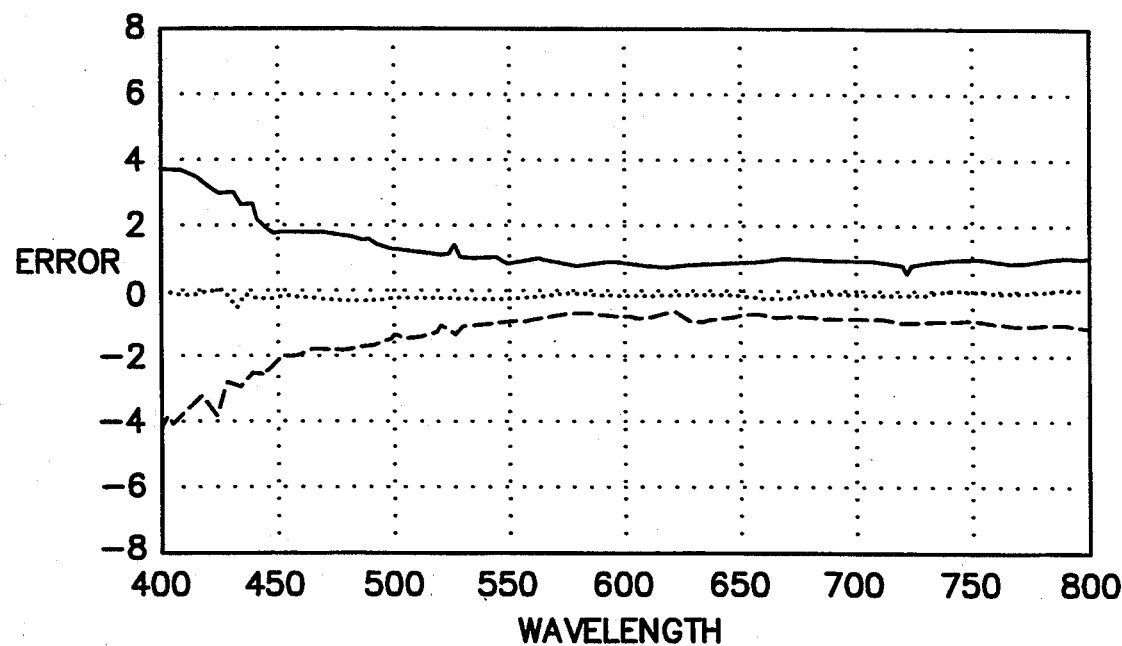
FIG. 13 is an error plot for color sensor No. 2 using normalization technique No. 2.

FIGS. 12 and 13 are error plots for two different sensors which use EQ. 1 and EQ. 2 as normalization models. Sensor no. 1 is shown in FIG. 12 while sensor no. 2 is shown in FIG. 13. For each sensor, EQ. 2 is held constant while EQ. 1 is updated using the reflective targets. As can be seen the error in both plots is minimal, especially compared to the error shown in FIG. 10.

The foregoing is a description of a novel and non-obvious method and apparatus for normalizing data. The applicants do not intend to limit the invention through the foregoing description, but instead define the invention through the claims appended hereto.

We claim:

1. A method of normalizing spectral data in an optical sensor comprising the steps of:

providing a light illuminating and sensing means which outputs a signal proportional to the magnitude of the reflectivity of an object or substance which is being scanned by the optical sensor;

providing at least one model manipulating means constructed with reference to testing of the light illuminating and sensing means for normalizing the output signal for a plurality of parameters which affect performance of the light illuminating and sensing means;

illuminating the object or substance with light emitted from the light illuminating and sensing means;

receiving light reflected off the object or substance and transmitting the reflected light to the light illuminating and sensing means;

generating the proportional output signal;

normalizing said proportional output signal through insertion of magnitude values of said signal into the normalization model manipulating means;

periodically receiving reflected light of known and different reflectivities so that known magnitudes of said output signal are produced; and updating the normalization model manipulating means based on any change in magnitude of said output signal produced from said reflected light of known and different reflectivities.

2. The method of normalizing spectral data in an optical sensor of claim 1, wherein the light illuminating and sensing means is a color sensor.

3. The method of normalizing spectral data in an optical sensor of claim 2, wherein the parameters are signal measurement values representing actual object or substance reflectivity, integration time, ambient temperature, and color temperature and lamp intensity.

4. The method of normalizing spectral data in an optical sensor of claim 3, wherein a first order polynomial is used as the mathematical model for the object or substance reflectivity and the color sensor integration time.

5. The method of normalizing spectral data in an optical sensor of claim 4, wherein a second order polynomial is used as the mathematical model for the ambient temperature.

6. The method of normalizing spectral data in an optical sensor of claim 5, wherein a second order polynomial is used as the mathematical model for the color temperature and lamp intensity.

7. The method of normalizing spectral data in an optical sensor of claim 6, wherein the mathematical model for the integration time and the actual object or substance reflectivity is periodically updated using a first and a second target of known and different reflectivities, while the mathematical models for the ambient temperature and the color temperature and lamp intensity are held constant.

8. The method of normalizing spectral data in an optical sensor of claim 1, wherein the object or substance is wood pulp.

9. The method of normalizing spectral data in an optical sensor of claim 1 wherein the reflected light of known and different reflectivities is received from at least one remotely positioned target.

10. Apparatus for normalization of spectral data in an optical sensor comprising:
a light emitting means;
a light receiving means;
a light sensing means connected to said light receiving means which outputs spectral data proportional to the intensity of the light transmitted to the light sensing means through the light receiving means;
at least one reflective target of a known reflectivity movably mounted remote from said light receiving means which when moved into the view of the light emitting means reflects light from said light emitting means into said light receiving means; and
processing means connected to said light sensing means which provides a normalization model for each of a plurality of parameters which affects the signal output from the light receiving means and which periodically updates the normalization models in response to light reflected off said targets.

11. The optical sensor of claim 10, wherein the light emitting means and the light receiving means are a single fiber-optic bundle.

12. The optical sensor of claim 10, wherein the light sensing means is a color sensor.

13. The optical sensor of claim 10, wherein said processing means is a microprocessor having a memory device associated therewith.

14. The optical sensor of claim 10, further comprising at least one other of said reflective targets having known and different reflectivities from the first at least one reflective targets, moveably positioned remote from said light receiving means to provide two known and different reflectivities when moved into the view of the light emitting means.

15. The optical sensor of claim 14, wherein each of the reflective targets is moveable through use of a solenoid.

16. The optical sensor of claim 14, wherein each of the reflective targets is moveable manually.

17. The optical sensor of claim 10, wherein the parameters are object or substance reflectivity, integration time, ambient temperature, and color temperature and lamp intensity.

18. The optical sensor of claim 16 wherein the normalization models for the object or substance reflectivity and integration time are first order polynomials.

19. The optical sensor of claim 17 wherein the normalization models for the ambient temperature and the color temperature are second order polynomials.

* * * * *